US010039763B2

(12) United States Patent
Aburatani et al.

(10) Patent No.: US 10,039,763 B2
(45) Date of Patent: Aug. 7, 2018

(54) PHARMACEUTICAL PREPARATION COMPRISING PHENYLALANINE DERIVATIVE

(71) Applicant: EA Pharma Co., Ltd., Tokyo (JP)

(72) Inventors: Satoshi Aburatani, Yokkaichi (JP);
Hirokazu Hagio, Kawasaki (JP);
Hiroyuki Higuchi, Hachioji (JP);
Kenichi Ogawa, Shirakawa (JP)

(73) Assignee: EA Pharma Co., Ltd., Tokyo (JP)

( * ) Notice: Subject to any disclaimer, the term of this patent is extended or adjusted under 35 U.S.C. 154(b) by 0 days.

(21) Appl. No.: 13/632,514

(22) Filed: Oct. 1, 2012

(65) Prior Publication Data
US 2013/0030013 A1 Jan. 31, 2013

Related U.S. Application Data

(63) Continuation of application No. PCT/JP2011/057799, filed on Mar. 29, 2011.

(30) Foreign Application Priority Data

Mar. 29, 2010 (JP) ................. 2010-074740

(51) Int. Cl.
*A61K 31/517* (2006.01)
*A61P 1/00* (2006.01)
*A61P 29/00* (2006.01)
*A61K 9/20* (2006.01)
*A61K 9/28* (2006.01)

(52) U.S. Cl.
CPC .......... *A61K 31/517* (2013.01); *A61K 9/2027* (2013.01); *A61K 9/2054* (2013.01); *A61K 9/2077* (2013.01); *A61K 9/2866* (2013.01)

(58) Field of Classification Search
USPC .................................................... 514/266.3
See application file for complete search history.

(56) References Cited

U.S. PATENT DOCUMENTS

| 2003/0220268 A1 | 11/2003 | Making et al. |
| 2006/0009476 A1 | 1/2006 | Kataoka et al. |
| 2006/0127475 A1 | 6/2006 | Makino et al. |
| 2006/0204572 A1 | 9/2006 | Higuchi et al. |
| 2006/0204574 A1 | 9/2006 | Ogawa et al. |
| 2006/0223836 A1 | 10/2006 | Making et al. |
| 2007/0018172 A1 | 1/2007 | Takahashi et al. |
| 2010/0137593 A1 | 6/2010 | Takahashi et al. |
| 2010/0204505 A1 | 8/2010 | Kataoka et al. |
| 2011/0065918 A1 | 3/2011 | Makino et al. |

FOREIGN PATENT DOCUMENTS

| CN | 1882346 A | 12/2006 |
| EP | 1 683 524 | 7/2006 |
| JP | 2000-355540 A | 12/2000 |
| JP | 2007-056011 A | 3/2007 |
| WO | WO 02/16329 | 2/2002 |
| WO | WO 2004/074264 | 9/2004 |
| WO | WO 2005/013964 A1 | 2/2005 |
| WO | WO 2005/046696 | 5/2005 |
| WO | WO 2005/046697 | 5/2005 |
| WO | WO 2005/051925 | 6/2005 |

OTHER PUBLICATIONS

U.S. Appl. No. 13/632,474, filed Oct. 1, 2012, Kataoka, et al.
"Pharmaceutical Applications of Solid Dispersion Systems", J. Pharm. Sci., vol. 60, No. 9, Sep. 1971, pp. 1281-1302.
Revised Handbook of Drug Additives, 2007, pp. 280-282 (w/English Translation).
Cyclopedia of Drug Additives, 2007, p. 93 (w/English Translation).
Written Opinion in International Application No. PCT/JP2011/057799, dated May 24, 2011. (w/English Translation).
Chinese Office Action dated Nov. 26, 2013, in China Patent Application No. 201180026703.6.
U.S. Appl. No. 14/206,540, filed Mar. 12, 2014, Kataoka, et al.
U.S. Appl. No. 13/632,514, filed Oct. 1, 2012, Aburatani, et al.
Office Action in corresponding European Patent Application No. 11762844.6, dated Apr. 11, 2014.
Office Action in Japanese Patent Application No. 2012-508342, dated Apr. 6, 2015. (w/English translation).
Crospovidone, Handbook of Pharmaceutical Excipients, 2002, p. 184, XP002719370.
Office Action dated Sep. 20, 2016 in the corresponding Japanese Patent Application No. 2015-147514 (with English Translation).
Japanese Office Action dated Jan. 30, 2017, in Japanese Patent Application No. 2015-147514 (with English Translation).

*Primary Examiner* — Kathrien A Cruz
(74) *Attorney, Agent, or Firm* — Oblon, McClelland, Maier & Neustadt, L.L.P.

(57) ABSTRACT

The disclosed pharmaceutical preparation comprises a compound represented by the chemical formula (A) or a pharmaceutically acceptable salt thereof, which is dispersed in a matrix consisting of a water-soluble high molecular weight substance; and Crospovidone:

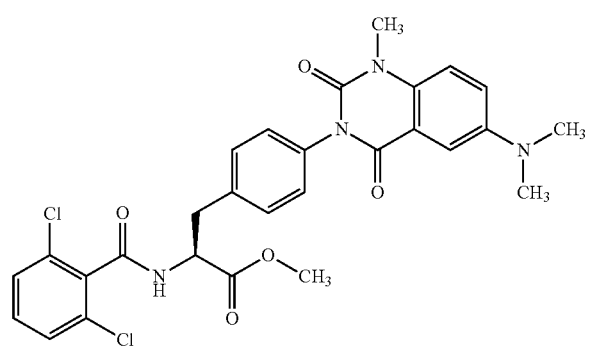

(A)

The pharmaceutical preparation is excellent in the solubility and the storage stability even if the amount of the compound or the salt included in each individual dosage unit is increased.

17 Claims, No Drawings

PHARMACEUTICAL PREPARATION COMPRISING PHENYLALANINE DERIVATIVE

TECHNICAL FIELD

The present invention relates to a pharmaceutical preparation comprising a phenylalanine derivative or a pharmaceutically acceptable salt thereof, which shows an α 4-integrin-inhibitory action and which is useful as a therapeutic agent for treating diseases such as inflammatory intestinal diseases.

BACKGROUND ART

Up to now, it has been known that a solid dispersion is formed by the dispersion of a drug hardly soluble in water in a polymer material to thus improve the solubility and easy absorbability of the drug. For instance, Griseofulvin is dispersed in a polyethylene glycol polymer as a water-soluble high molecular weight substance to give a solid dispersion for the improvement of, for instance, the solubility of the drug (see Non-Patent Document 1 specified bellow).

The compound represented by the chemical formula (A) as will be specified below or a pharmaceutically acceptable salt thereof, which is a subject of the present invention, is a compound or a salt, which shows an α 4-integrin-inhibitory action and which is useful as a therapeutic agent for treating diseases such as inflammatory, intestinal diseases and the compound or the salt can be produced according to the description disclosed in Patent Documents 1 and 2 specified below.

In addition, Patent Document 3 discloses a pharmaceutical preparation in the form of a solid dispersion which comprises, as effective components, wide variety of phenylalanine derivatives including the compound represented by the chemical formula (A), or pharmaceutically acceptable salts thereof and whose solubility and absorbability are improved. Moreover, Patent Document 4 discloses a sustained release type orally administrable pharmaceutical preparation.

In the pharmaceutical preparation containing the compound represented by the chemical formula (A) as an effective component, it would sometimes be necessary to increase the amount of the effective component to be incorporated into each individual dosage unit for satisfying a variety of requirements and for this reason, there has been desired for the development of a pharmaceutical preparation which is further improved in the solubility and the storage stability of the preparation in order to cope with such situations.

PRIOR ART LITERATURE

Patent Document

Patent Document 1: Pamphlet of International Patent Laid-Open No. 02/16329;
Patent Document 2: Pamphlet of International Patent Laid-Open No. 2004/074264;
Patent Document 3: Pamphlet of International Patent Laid-Open No. 2005/46696;
Patent Document 4: Pamphlet of International Patent Laid-Open No. 2005/46697; and
Patent Document 5: Pamphlet of International Patent Laid-Open No. 2005/051925.

Non-Patent Document

Non-Patent Document 1: J. Pharm. Sci., 1971, 60, 9, pp. 1281-1302.

DISCLOSURE OF THE INVENTION

It is thus an object of the present invention to provide a pharmaceutical preparation comprising the compound represented by the chemical formula (A) or a pharmaceutically acceptable salt thereof, which is excellent in the solubility and the storage stability even if the amount of the compound or the salt included in each individual dosage unit is increased.

The inventors of this invention have conducted various investigations to solve the aforementioned problems associated with the conventional techniques, and as a result, have found that if using Crospovidone, as a disintegrator, which is not specifically disclosed in Patent Document 3, the aforementioned problems can efficiently be solved, and have thus completed the present invention.

In other words, the present invention herein provides a pharmaceutical preparation comprising the compound represented by the chemical formula (A) or a pharmaceutically acceptable salt thereof, which is dispersed in a matrix consisting of a water-soluble high molecular weight substance; and Crospovidone:

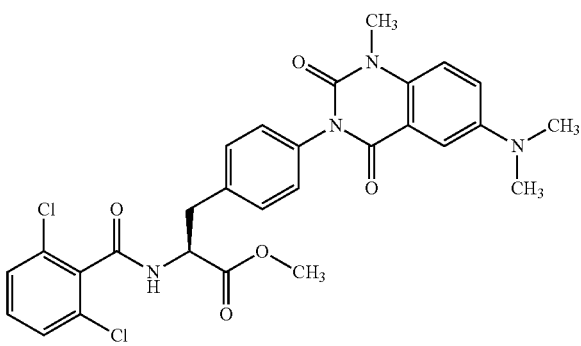

(A)

MODE FOR CARRYING OUT THE INVENTION

The compound represented by the chemical formula (A), which is used as an effective component in the pharmaceutical preparation according to the present invention, is the compound described in Example 196 of WO 02-16329 (Patent Document 1). This will hereunder be simply referred to as "the compound (A)" as well.

This compound can be prepared according to the methods disclosed in Patent Document 1 and Patent Document 2 (Example 1).

As the pharmaceutically acceptable salts of the compound (A), there may be listed, for instance, acid-addition salts with inorganic acids (such as hydrochloric acid, sulfuric acid and phosphoric acid); acid-addition salts with organic carboxylic acids (such as acetic acid, citric acid, benzoic acid, maleic acid, fumaric acid, tartaric acid and succinic acid); and acid-addition salts with organic sulfonic acids (such as methane-sulfonic acid and p-toluene-sulfonic acid). Examples of methods for forming such a salt include a method which comprises the step of blending the compound represented by the chemical formula (A) with an acid or a base required for the formation of an intended salt in a solvent or dispersant, in an appropriate ratio, and a method which comprises the step of subjecting, to a cation- or anion-exchange treatment, a salt of the compound (A) other than the intended one.

In addition, it is a matter of course that the compound (A) according to the present invention likewise includes, for instance, a solvate thereof such as a hydrate as well as an addition product thereof with an alcohol.

Moreover, Patent Document 5 discloses crystals of the compound (A) and these crystals can likewise be used as raw materials for the production of the pharmaceutical preparations according to the present invention.

In the pharmaceutical preparation according to the present invention, the compound represented by the chemical formula (A) or a pharmaceutically acceptable salt thereof is dispersed in a matrix consisting of a water-soluble high molecular weight substance. In this connection, it is preferred that the compound (A) in its amorphous state is dispersed in the water-soluble polymer.

The water-soluble high molecular weight substance used in the present invention is not restricted to any particular one inasmuch as it is a water-soluble polymeric substance and it can certainly dissolve or disperse, therein, the compound (A) or a pharmaceutically acceptable salt thereof and usable herein as such high molecular weight substances may be a variety of synthetic polymers and naturally occurring polymers. Specific examples of these water-soluble high molecular weight substances, preferably used in the present invention, include celluloses and derivatives thereof (for instance, methyl cellulose, Hypromellose (another name: hydroxypropyl-methyl cellulose), hydroxypropyl cellulose, hydroxy-propylmethyl cellulose phthalate, hydroxypropylmethyl cellulose acetate succinate, carboxymethyl cellulose, sodium carboxymethyl cellulose, hydroxyethyl cellulose, and cellulose acetate phthalate); synthetic polymers (for instance, polyethylene glycol, polyvinyl alcohol, polyvinyl pyrrolidone, polyvinyl-acetal diethylamino acetate, aminoalkyl methacrylate copolymer E, aminoalkyl methacryl copolymer RS, methacrylic acid copolymer L, methacrylic acid copolymer LD, methacrylic acid copolymer S, and carboxy-vinyl copolymer); naturally occurring polymers and saccharides (for instance, gum Arabic, sodium alginate, alginic acid propylene glycol ester, agar, gelatin, tragacanth gum, and xanthane gum).

Among them, preferably used herein as such water-soluble high molecular weight substances include, for instance, methyl cellulose, Hypromellose, hydroxypropyl cellulose, polyethylene glycol, polyvinyl alcohol, and polyvinyl pyrrolidone, and more preferably used herein as such substances are methyl cellulose and Hypromellose, among others.

These high molecular weight substances may be used alone or in any combination of at least two of them.

In the pharmaceutical preparation according to the present invention, the amount of the water-soluble polymer substance relative to that of the compound (A) is so selected that the amount of the polymer substance ranges from 0.1 to 10 part by mass, preferably 0.5 to 5 parts by mass and more preferably 1 to 3 parts by mass per one part by mass of the compound (A).

In addition, the content of the compound (A), in the pharmaceutical preparation according to the present invention, preferably ranges from 14 to 40% by mass, more preferably 22 to 38% by mass and further preferably 28 to 35% by mass.

The compound (A) or a pharmaceutically acceptable salt thereof dispersed in such a water-soluble polymer matrix can be prepared according to a method selected from the solvent method, the melting method, the melt kneading method under heating and pressing, or the mixing and pulverizing method.

The solvent method is a technique which comprises the steps of dissolving or dispersing the compound (A) or a pharmaceutically acceptable salt thereof in an organic solvent in combination with a water-soluble high molecular weight substance and then removing the organic solvent according to the usual technique to thus make the compound (A) or the salt thereof adsorb on the water-soluble high molecular weight substance.

As methods for dissolving or dispersing the compound (A) or a salt thereof and a water-soluble high molecular weight substance in an organic solvent, there can be listed, for instance, those specified below:

(i) A method comprising the steps of dissolving or dispersing only the compound (A) or a pharmaceutically acceptable salt thereof in an organic solvent and then dispersing the resulting solution or dispersion in a water-soluble high molecular weight substance; and (ii) A method comprising the step of dissolving or dispersing the compound (A) or a pharmaceutically acceptable salt thereof in an organic solvent in combination with a water-soluble high molecular weight substance.

The organic solvent used in the solvent method is not restricted to any particular one inasmuch as the compound (A) or a pharmaceutically acceptable salt thereof can be dissolved or dispersed therein. Specific examples of such organic solvents include aliphatic halogenated hydrocarbons (such as dichloromethane, dichloroethane and chloroform); alcohols (such as methanol, ethanol and propanol); ketones (such as acetone and methyl ethyl ketone); ethers (such as diethyl ether and dibutyl ether); aliphatic hydrocarbons (such as n-hexane, cyclohexane and n-heptane); aromatic hydrocarbons (such as benzene, toluene and xylene); organic acids (such as acetic acid and propionic acid); esters (such as ethyl acetate); amides (such as dimethylformamide and dimethyl-acetamide); nitriles (such as acetonitrile and propionitrile); and mixed solvents comprising the foregoing organic solvents. Among these organic solvents, preferably used herein include, for instance, halogenated hydrocarbons, alcohols and mixed solvents comprising these solvents. Further preferably used herein are, for instance, dichloromethane, methanol, ethanol and mixture thereof.

The organic solvents likewise usable in the solvent method further include, for instance, mixtures each comprising the foregoing organic solvent and water.

The foregoing melting method herein used is a method comprising the steps of dissolving or dispersing, with heating, the compound (A) or a pharmaceutically acceptable salt thereof in a water-soluble high molecular weight substance and then cooling the resulting solution or dispersion. An example of such a method for dissolving or dispersing the compound (A) or the salt thereof in a water-soluble high molecular weight substance includes one which comprises the step of stirring these components, while heating them at a temperature of not less than the melting point or softening point of the compound (A) or the pharmaceutically acceptable salt thereof or the water-soluble polymer. In this case, additives may be incorporated into the foregoing components. Examples of such additives are plasticizers (such as polyethylene glycol, sucrose fatty acid esters, glycerin fatty acid esters, propylene glycol, triethyl citrate, castor oil and glycerin triacetate); and surfactants (such as sodium lauryl sulfate, Polysorbate 80, sucrose fatty acid esters, Polyoxy 40 Stearate, polyoxyethylene hardened castor oil 60, sorbitan mono-stearate and sorbitan mono-palmitate).

The production of a pharmaceutical preparation in the form of a solid dispersion according to the melting method can be carried out through the use of, for instance, a stirring granulator provided with a heating means.

More specifically, a mixture is preliminarily prepared, which comprises the compound (A) or a pharmaceutically acceptable salt thereof and a water-soluble high molecular weight substance. To this mixture, there may be added additives such as the aforementioned plasticizer and/or surfactant, as the need arises. The conditions such as the processing temperature and the processing time period may vary depending on the kinds of, for instance, the compound, water-soluble high molecular weight substance and additives to be used, but the processing temperature in general ranges from room temperature to 300° C., while the processing time period in general falls within the range of from several minutes to ten and several hours. In addition, the cooling time period usually falls within the range of from −100 to room temperature.

The foregoing melt kneading method under heating and pressing herein used means a method comprising the step of mixing the compound (A) or a pharmaceutically acceptable salt thereof and a water-soluble high molecular weight substance while heating and pressing these components. In this method, the processing conditions such as the rotational frequency of the processing screw, the processing temperature and the processing time period may vary depending on the kinds of, for instance, the compound, water-soluble high molecular weight substance and additives to be used, but the rotational frequency of the processing screw in general ranges from 10 to 500 rpm, the processing temperature in general ranges from room temperature to 300° C. and the processing time period in general falls within the range of from several minutes to ten and several hours. The production of a solid dispersion according to the melt kneading method under heating and pressing can be carried out using, for instance, a twin-screw extruder or a kneader, provided with a heating device. More specifically, such a solid dispersion can be prepared, for instance, according to the following procedures:

The compound (A) or a pharmaceutically acceptable salt thereof and a water-soluble high molecular weight substance as well as the foregoing additives, which are used as the need arises, are preliminarily blended together. The resulting mixture is fed to a melt kneading device provided with a heating means and a pressurizing means at a powder-feed rate ranging from 10 to 200 g/min. The kneading process is carried out at a rotational frequency of the processing screw ranging from 50 to 300 rpm and a processing temperature ranging from 25 to 300° C. This plastic-like solid dispersion is then pulverized by the use of a pulverizer to thus give a desired solid dispersion.

The foregoing mixing and pulverizing method herein used means a method which comprises the steps of blending the compound (A) or a pharmaceutically acceptable salt thereof with a water-soluble high molecular weight substance and then pulverizing the resulting mixture in such a manner that the compound (A) or the salt thereof is dispersed in its amorphous state.

The blending and pulverizing operations can be carried out according to the usual technique while using a blending machine and a pulverizer. In this respect, the pulverization of the water-soluble high molecular weight substance and the compound (A) is preferably carried out using, for instance, a cutter mill, a ball mill, a hammer mill or a mortar.

The pharmaceutical preparation according to the present invention is characterized in that it further comprise Crospovidone in addition to the compound represented by the foregoing chemical formula (A) or a pharmaceutically acceptable salt thereof which is dispersed in the matrix consisting of the foregoing water-soluble high molecular weight substance.

Crospovidone is also referred to as "1-ethenyl-2-pyrrolidinone homopolymer" as another name and it is a cross-linked polymeric material of 1-vinyl-2-pyrrolidone. This substance is white to pale yellow-colored powder and hardly soluble in water. In the present invention, Crospovidone is used as a disintegrator. The amount of Crospovidone used herein preferably ranges from 0.1 to 20% by mass and more preferably 1 to 15% by mass on the basis of the total mass of the pharmaceutical preparation.

In the present invention, Crospovidone may further be used in combination with one or at least two other disintegrators selected from the group consisting of hydroxypropyl cellulose, hydroxypropyl cellulose having a low degree of substitution, sodium Cros-carmellose, pregelatinized starch (such as partially pregelatinized starch), methyl cellulose, sodium alginate, sodium carboxymethyl starch, calcium carmellose, sodium carmellose, crystalline cellulose and crystalline cellulose/sodium carmellose. Among them, sodium Cros-carmellose is preferably used in combination with Crospovidone. In this case, sodium Cros-carmellose is used in combination in such an amount that it falls within the tolerated range with respect to the total mass of the pharmaceutical preparation or in an amount ranging from 10 to 1,000 parts by mass and more preferably 50 to 600 parts by mass per 100 parts by mass of Crospovidone.

When preparing the pharmaceutical preparation according to the present invention, the following additives may likewise be incorporated into the pharmaceutical preparation as the need arises: Specific examples of such additives include excipients [for instance, saccharides (such as lactose, sucrose, glucose, reducing maltose, mannitol, sorbitol, xylitol, and trehalose); starches and derivatives thereof (such as pregelatinized starch (for instance, partially pregelatinized starch), dextrin, pullulan, corn starch and potato starch); celluloses (such as crystalline cellulose, microcrystalline cellulose, crystalline cellulose/sodium carmellose and hydroxypropyl cellulose); magnesium metasilicate aluminate, silicon dioxide, light anhydrous silicic acid and amino acids]; coloring agents; corrigents (such as sucrose, aspartame, mannitol, dextran, saccharin, menthol, citric acid, tartaric acid, malic acid, ascorbic acid, sweet hydrangea leaf, fennel, ethanol, fructose, xylitol, glycyrrhizic acid, purified sucrose, L-glutamic acid and cyclodextrin); lubricants (such as magnesium stearate, talc, light anhydrous silicic acid, calcium stearate, magnesium oxide, magnesium lauryl sulfate and magnesium metasilicate aluminate); and surfactants (such as sodium lauryl sulfate, Polysorbate 80, sucrose fatty acid esters, Polyoxy 40 Stearate, polyoxyethylene hardened castor oil 60, sorbitan mono-stearate and sorbitan mono-palmitate). Moreover, it is also possible to incorporate a foaming agent (such as sodium hydrogen carbonate or ammonium carbonate) or the like into the pharmaceutical preparation of the present invention.

It is preferred that the pharmaceutical preparation of the present invention comprises, as the foregoing excipient, at least one member selected from the group consisting of mannitol, pregelatinized starches (such as partially pregelatinized starches) and crystalline celluloses.

The pharmaceutical preparation of the present invention is preferably produced by granulating a dispersion consisting of the compound (A) or a pharmaceutically acceptable salt thereof, which is dispersed in a matrix of a water-soluble high molecular weight substance, in combination with the foregoing additional components such as a disintegrator and/or an excipient. In this connection, the following two steps may continuously or integrally be carried out: a step of making the foregoing compound (A) or the pharmaceutically acceptable salt thereof disperse in and adsorb on the water-soluble high molecular weight substance; and a step of granulating the foregoing additional components such as a disintegrator and/or an excipient. In this respect, preferred examples of such methods include one which comprises the steps of dissolving the compound (A) or a pharmaceutically acceptable salt thereof in an organic solvent, dissolving or dispersing a water-soluble high molecular weight substance in the organic solvent, blending or granulating the resulting solution or dispersion in combination with auxiliary agents such as an excipient and/or disintegrator using a device such as a stirring and granulating device, a fluidized bed granulating device, a spray drying device, Bohle Container Mixer, or a V-shaped blending device, and then removing the organic solvent through the distillation under reduced or ordinary pressure according to the usual technique; or one which comprises the steps of dissolving a water-soluble high molecular weight substance in an organic solvent, further dissolving or dispersing the compound (A) or a pharmaceutically acceptable salt thereof in the organic solvent, blending or granulating the resulting liquid in combination with auxiliary agents such as an excipient and/or disintegrator using a device such as a stirring and granulating device, a fluidized bed granulating device, a spray drying device, Bohle Container Mixer, or a V-shaped blending device, and then removing the organic solvent through the distillation under reduced or ordinary pressure according to the usual technique.

The organic solvent can be removed from the resulting particulate material by, for instance, drying the material under reduced pressure or drying the same with heating. The conditions such as the processing pressure, the processing temperature and the processing time period may vary depending on the kinds of, for instance, the compound, water-soluble high molecular weight substance and organic solvent to be used, but the processing pressure in general ranges from 1 mmHg to ordinary pressure, the processing temperature in general ranges from room temperature to 250° C. and the processing time period in general falls within the range of from several minutes to several days.

In the foregoing method, the foregoing compound (A) or a pharmaceutically acceptable salt thereof is dispersed in and adsorbed on a water-soluble high molecular weight substance to give a mixture and then the organic solvent is removed from the mixture through distillation. The mixture thus prepared can be used as a powder, a fine granule or a granule without any further treatment, but it may further be subjected to various steps (such as a mixing step, a granulating step, a kneading step, a compressing or tabletting step, a capsule-filling step and/or a coating step) to thus give a pharmaceutical preparation in the form of, for instance, a tablet or a coating tablet. At this stage, Crospovidone may be incorporated into the mixture obtained after the foregoing step for the removal of the organic solvent through distillation, or it may likewise be added to the pharmaceutical preparation during the step for the preparation of the latter.

When preparing the pharmaceutical preparation according to the present invention in the form of a tablet, the mixture, which is prepared according to the method in which the foregoing compound (A) or a pharmaceutically acceptable salt thereof is dispersed in and adsorbed on a water-soluble high molecular weight substance and from which the organic solvent is removed through distillation, may be sent to the tabletting step without any particular pretreatment, but it would be preferred that at least part of the disintegrator to be incorporated into the pharmaceutical preparation of the present invention is set aside or retained, thereafter it is blended with the foregoing mixture prior to the tabletting step and then the tabletting step is initiated. In this respect, it is particularly preferred that the whole amount of Crospovidone is set aside, it is blended with the foregoing mixture prior to the tabletting step and then this final mixture is subjected to a tabletting step. In this connection, it is further preferred that the whole amount of the lubricant is set aside as well, it is blended with the foregoing mixture along with Crospovidone prior to the tabletting step and then the final mixture is subjected to a tabletting step.

According to the present invention, it is also possible to prepare a coating tablet by first preparing a tablet and subsequently applying a coating agent onto the surface of the tablet.

Such a coating agent is not restricted to any particular one inasmuch as it is a coating agent which has currently been used in this field of forming pharmaceutical preparations and specific examples thereof include acrylic acid derivatives (such as methacrylic acid copolymer L, methacrylic acid copolymer S, methacrylic acid copolymer LD, and aminoalkyl methacrylate copolymer E); cellulose derivatives (such as hydroxypropyl-methyl cellulose phthalate, hydroxypropyl-methyl cellulose acetate succinate, carboxy-methylethyl cellulose, cellulose acetate phthalate, hydroxyethyl cellulose, hydroxypropyl cellulose, hypromellose, methyl cellulose, methyl-hydroxyethyl cellulose, Opadry, calcium carmellose and sodium carmellose); vinyl derivatives (such as polyvinyl pyrrolidone, polyvinyl alcohol and polyvinyl acetal diethylamino acetate); starches (such as dextrin and pullulan); and naturally occurring polymers and saccharides (such as shellac, gelatin, agar and gum Arabic). These coating agents may be used alone or in any combination of at least two of them.

Water-soluble polymers are preferably used as such coating agents and particularly preferably used herein include, for instance, aminoalkyl methacrylate copolymer E, hypromellose, methyl cellulose, methyl-hydroxyethyl cellulose, Opadry, calcium carmellose, sodium carmellose, polyvinyl pyrrolidone, polyvinyl alcohol, dextrin, pullulan, gelatin, agar and gum Arabic, among others.

In this connection, the coating agent is used in such an amount that it does not exert any substantially effect on the dissolution rate of the pharmaceutical preparation and accordingly, the rate of solid content covering the pharmaceutical preparation ranges, for instance, from 0.1 to 20% by mass, preferably 0.5 to 10% by mass and more preferably 1 to 7% by mass.

The compound (A) or a pharmaceutically acceptable salt thereof to be incorporated into the pharmaceutical preparation of the present invention shows an excellent α 4-integrin-inhibitory action and therefore, the pharmaceutical preparation of the present invention can be used as an excellent α 4-integrin-inhibitory agent. The pharmaceutical preparation can likewise efficiently be used as an effective component of a therapeutic agent or a prophylactic agent for treating or preventing either of inflammatory diseases, wherein the α 4-integrin-dependent leukocyte adhesion process is involved in the pathema, rheumatoid arthritis, inflammatory intestinal diseases (inclusive of, for instance, Crohn's disease and ulcerative colitis), systemic lupus erythematosus, disseminated or multiple sclerosis, Sjogren's syndrome, asthma, psoriasis, allergy, diabetes (mellitus), cardiovascular diseases, arterial sclerosis, restenosis, tumor hyperplasia, tumor metastasis and graft rejection.

Furthermore, the compound (A) or a pharmaceutically acceptable salt thereof may likewise be used in combination with other pharmaceutical agents which can show therapeutic and/or prophylactic effects on the foregoing diseases or disorders. For instance, in case of the inflammatory intestinal diseases such as Crohn's disease and ulcerative colitis, such other pharmaceutical agents include, for instance, an elemental diet (such as Elental available from Ajinomoto Co., Ltd.), 5-ASA pharmaceutical preparations (such as mesalazine, and salazosulfapyridine (sulfasalazine)), adrenocortical hormone-containing pharmaceutical preparations (such as prednisolone, bethamethasone, and budesonide), and antibacterial agents (such as metronidazole), among others. In addition, also listed as such other agents capable of being used in combination with the compound or salt of the present invention include, for instance, immunosuppressive agents (such as azathioprine, 6-mercaptoprine, ciclosporin, and tacrolimus). Moreover, anti-cytokine agents may likewise be used as such pharmaceutical agents capable of being used in combination with the foregoing. Specific examples thereof are anti-TNF α-antibodies (such as infliximab, adalimumab, certolizumab pegol, and golimumab), anti-IL-6 receptor antibodies (such as tocilizumab), anti-IL-12/23 antibodies (such as ustekinumab, and briakinumab), anti-IL-17 receptor antibodies (such as AMG827 and AIN457), IL-12/23 production-inhibitory agents (such as STA-5326) as low molecular weight agents and PDE-4-inhibitory agents (such as tetomilast). In addition, also listed herein as such other agents include, for instance, CCR9-inhibitory agents as the cellular infiltration-inhibitory agents (such as GSK1605786 and CCX025), and anti-α 4 β7-integrin antibodies (such as vedolizumab). Furthermore, usable herein in combination with the foregoing compounds or salts of the present invention also include other therapeutic methods which can show a therapeutic and/or prophylactic effect on the aforementioned diseases in addition to the foregoing pharmaceutical agents. For instance, in case of the inflammatory intestinal diseases such as Crohn's disease and ulcerative colitis, such therapeutic and/or prophylactic methods include, for instance, leukocyte-removing therapies (such as GCAP and LCAP).

In other words, the pharmaceutical preparation of the present invention can be used in combination with other pharmaceutical agents having an effect of treating and/or preventing the foregoing diseases. In addition, the pharmaceutical preparation of the present invention can likewise be used in combination with other therapeutic methods for the treatment of the foregoing diseases.

The pharmaceutical preparation according to the present invention will hereunder be described in more detail with reference to the following Examples.

Example 1

Methyl cellulose (SM-4, available from Shin-Etsu Chemical Co., Ltd.; 1,050 g) was completely wetted with methanol by the addition of 3,850 g of methanol, 15,400 g of dichloromethane was then added to the methanol-wetted methyl cellulose, followed by the stirring of the mixture for the dissolution of the methyl cellulose. Then 700 g of the compound (A) was added to the resulting methyl cellulose solution and the resulting mixture was stirred for the dissolution of the compound (A). The solution thus prepared was used as a spray liquid as will be described below. To a fluidized bed-type granulator (FLO-5 available from Freund Sangyo Co., Ltd.), there were charged 269 g of PCS PC-10 (partially pregelatinized starch, available from Asahi Kasei Chemicals Co., Ltd.), 230 g of Ac-Di-Sol (sodium Croscarmellose, available from Dainippon Sumitomo Pharmaceuticals Co., Ltd.), 403 g of CEOLUS PH-102 (crystalline cellulose available from Asahi Kasei Chemicals Co., Ltd.), and 217 g of Mannite P (mannitol, available from Mitsubishi Shoji Food Tech Co., Ltd.), followed by the blending and drying of these components. Then 20,160 g of the foregoing spray liquid was sprayed on the dried mixture, while the mixture was subjected to fluidized bed-granulation. After the completion of the spraying operation, the granulated mixture was dried in the fluidized bed-type granulator to give granules. To 100 parts by mass of the resulting granules, there were added to and blended with 2.0 parts by mass of Crospovidone (available from TSP Japan Co., Ltd.) and 0.5 parts by mass of magnesium stearate (available from Taiheiyo Chemical Industry Co., Ltd.) and then the resulting blend was compressed into uncoated tablets. In addition, the resulting uncoated tablets were coated with a film of hypromellose (coated amount: 4.7% by mass on the basis of the total mass of the pharmaceutical preparation) to thus give the intended pharmaceutical preparation in the form of tablets each containing the compound (A) in an amount of 120 mg per tablet.

Example 2

Methyl cellulose (SM-4, available from Shin-Etsu Chemical Co., Ltd.; 1,104 g) was completely wetted with methanol by the addition of 3,267 g of methanol, 13,069 g of dichloromethane was then added to the methanol-wetted methyl cellulose, followed by the stirring of the mixture for the dissolution of the methyl cellulose. Then 960 g of the compound (A) was added to the resulting methyl cellulose solution and the resulting mixture was stirred for the dissolution of the compound (A). The solution thus prepared was used as a spray liquid as will be described later. To a fluidized bed-type granulator (FLO-5 available from Freund Sangyo Co., Ltd.), there were charged 200 g of PCS PC-10 (partially pregelatinized starch, available from Asahi Kasei Chemicals Co., Ltd.), 240 g of Ac-Di-Sol (sodium Croscarmellose, available from Dainippon Sumitomo Pharmaceuticals Co., Ltd.), 360 g of CEOLUS PH-102 (crystalline cellulose available from Asahi Kasei Chemicals Co., Ltd.), and 120 g of Mannite P (mannitol, available from Mitsubishi Shoji Food Tech Co., Ltd.), followed by the blending and drying of these components. Then 18,400 g of the foregoing spray liquid was sprayed on the dried mixture, while the mixture was subjected to fluidized bed-granulation. After the completion of the spraying operation, the granulated mixture was dried in the fluidized bed-type granulator to give granules. To 100 parts by mass of the resulting granules, there were added to and blended with 2.7 parts by mass of Crospovidone (available from ISP Japan Co., Ltd.) and 0.5 parts by mass of magnesium stearate (available from Taiheiyo Chemical Industry Co., Ltd.) and then the resulting blend was compressed into uncoated tablets. In addition, the resulting uncoated tablets were coated with a film of hypromellose (coated amount: 4.7% by mass on the basis of the total mass of the pharmaceutical preparation) to thus give the intended pharmaceutical preparation in the form of tablets each containing the compound (A) in an amount of 240 mg per tablet.

Example 3

Methyl cellulose (SM-4, available from Shin-Etsu Chemical Co., Ltd.; 1,200 g) was completely wetted with methanol by the addition of 3,568 g of methanol, 14,272 g of dichloromethane was then added to the methanol-wetted methyl cellulose, followed by the stirring of the mixture for the dissolution of the methyl cellulose. Then 960 g of the compound (A) was added to the resulting methyl cellulose solution and the resulting mixture was stirred for the dissolution of the compound (A). The solution thus prepared was used as a spray liquid as will be described later. To a fluidized bed-type granulator (FLO-5 available from Freund Sangyo Co., Ltd.), there were charged 148 g of PCS PC-10 (partially pregelatinized starch, available from Asahi Kasei Chemicals Co., Ltd.), 176 g of Ac-Di-Sol (sodium Croscarmellose, available from Dainippon Sumitomo Pharmaceuticals Co., Ltd.), 224 g of CEOLUS PH-102 (crystalline cellulose available from Asahi Kasei Chemicals Co., Ltd.), and 76 g of Mannite P (mannitol, available from Mitsubishi Shoji Food Tech Co., Ltd.), followed by the blending and drying of these components. Then 20,000 g of the foregoing spray liquid was sprayed on the dried mixture, while the mixture was subjected to fluidized bed-granulation. After the completion of the spraying operation, the granulated mixture was dried in the fluidized bed-type granulator to give granules. To 100 parts by mass of the resulting granules, there were added to and blended with 8.6 parts by mass of Crospovidone (available from ISP Japan Co., Ltd.) and 0.6 parts by mass of magnesium stearate (available from Taiheiyo Chemical Industry Co., Ltd.) and then the resulting blend was compressed into uncoated tablets. In addition, the resulting uncoated tablets were coated with a film of hypromellose (coated amount: 4.7% by mass on the basis of the total mass of the pharmaceutical preparation) to thus give the intended pharmaceutical preparation in the form of tablets each containing the compound (A) in an amount of 240 mg per tablet.

Example 4

A coated pharmaceutical preparation was prepared by repeating the same procedures used in Example 3 except that 10.1 parts by mass of Crospovidone was added to the resulting granules per 100 parts by mass of the granules to prepare an intended coated pharmaceutical preparation in the form of coating tablets.

Comparative Example 1

A pharmaceutical preparation was prepared by repeating the same procedures used in Example 3 except that any Crospovidone was not used for the preparation of uncoated tablets to thus coat the resulting granules and to thus obtain a pharmaceutical preparation in the form of coated tablets each containing 240 mg of the compound (A).

Comparative Example 2

Methyl cellulose (SM-4, available from Shin-Etsu Chemical Co., Ltd.; 966 g) was completely wetted with methanol by the addition of 2,859 g of methanol, 11,435 g of dichloromethane was then added to the methanol-wetted methyl cellulose, followed by the stirring of the resulting mixture for the dissolution of the methyl cellulose. Then 840 g of the compound (A) was added to the resulting methyl cellulose solution and the resulting mixture was stirred for the dissolution of the compound (A). The solution thus prepared was used as a spray liquid as will be described later. To a fluidized bed-type granulator (FLO-5 available from Freund Sangyo Co., Ltd.), there were charged 210 g of PCS PC-10 (partially pregelatinized starch, available from Asahi Kasei Chemicals Co., Ltd.), 182 g of Ac-Di-Sol (sodium Croscarmellose, available from Dainippon Sumitomo Pharmaceuticals Co., Ltd.), 315 g of CEOLUS PH-102 (crystalline cellulose available from Asahi Kasei Chemicals Co., Ltd.), and 168 g of Mannite P (mannitol, available from Mitsubishi Shoji Food Tech Co., Ltd.), followed by the blending and drying of these components. Then 16,100 g of the foregoing spray liquid was sprayed on the dried mixture, while the mixture was subjected to fluidized bed-granulation. After the completion of the spraying operation, the granulated mixture was dried in the fluidized bed-type granulator to give granules. To 100 parts by mass of the resulting granules, there was added to and blended with 0.5 parts by mass of magnesium stearate alone (available from Taiheiyo Chemical Industry Co., Ltd.) and then the resulting blend was compressed into uncoated tablets. In addition, the resulting uncoated tablets were coated with a film of hypromellose (coated amount: 4.7% by mass on the basis of the total mass of the pharmaceutical preparation) to thus give the intended pharmaceutical preparation in the form of coated tablets each containing 240 mg of the compound (A).

The pharmaceutical preparations thus prepared in the foregoing Examples and Comparative Examples were inspected for the dissolving ability and the storage stability according to the following methods.

Dissolving Ability (Initial Dissolving Ability)

The dissolving ability of each tablet prepared above was determined according to the puddle method (50 rpm) as specified in Japanese Pharmacopoeia, 15$^{th}$ Revised Edition, while using 900 mL of a solution for dissolution test (an acetic acid/sodium acetate buffer (0.05 mol/L) containing 0.5% (w/v) or 1.0% (w/v) sodium lauryl sulfate and having a pH value of 4.0). In this respect, the dissolution rate of the compound (A) was determined at 15 minutes, 30 minutes, 45 minutes and 60 minutes after the addition of each tablet to the solution for dissolution test (these data will hereunder be referred to as "15 min Value" and so forth).

Storage Stability (Dissolving Ability After Storage)

Each coating pharmaceutical preparation, in the form of a tablet, was stored at 60° C. over 2 weeks to one month, while the system was kept under airtight conditions and the humidity was left to follow its natural course. Then the dissolving ability of each tablet thus stored above was determined according to the puddle method (50 rpm) as specified in Japanese Pharmacopoeia, 15$^{th}$ Revised Edition, while using 900 mL of a solution for dissolution test (an acetic acid/sodium acetate buffer (0.05 mol/L) containing 0.5% (w/v) or 1.0% (w/v) sodium lauryl sulfate and having a pH value of 4.0). In this respect, the dissolution rate of the compound (A) was determined at 15 minutes, 30 minutes, 45 minutes and 60 minutes after the addition of each tablet to the solution for dissolution test (these data will hereunder be referred to as "15 min Value" and so forth).

The results thus obtained are summarized in the following Table 1:

TABLE 1

| (Unit: %) | Ex. 1 | Ex. 2 | Ex. 3 | Ex. 4 | Comp. Ex. 1 | Comp. Ex. 2 |
|---|---|---|---|---|---|---|
| Uncoated Tablet Portion | | | | | | |
| Compound (A) | 22.3 | 29.7 | 30.1 | 29.7 | 32.7 | 29.7 |
| Crospovidone | 1.9 | 2.5 | 7.5 | 8.7 | 0.0 | 0.0 |
| Auxiliary Raw Material | 71.1 | 63.1 | 57.7 | 56.9 | 62.6 | 65.6 |
| Coating Portion | 4.7 | 4.7 | 4.7 | 4.7 | 4.7 | 4.7 |
| Coating Pharmaceutical Preparation, Total Amount | 100 | 100 | 100 | 100 | 100 | 100 |
| Initial Dissolving Ability | | | | | | |
| 15 min Value | 62.7 | 60.0 | 68.0 | 54.8 | 6.7 | 59.9 |
| 45 min Value | 91.0 | 89.2 | 91.4 | 87.8 | 72.5 | 90.1 |
| Dissolving Ability After Storage | | | | | | |
| 15 min Value | 64.1 | 66.1 | 66.6 | 74.2 | 69.0 | 50.8 |
| 45 min Value | 90.1 | 89.0 | 77.8 | 87.9 | 91.2 | 62.4 |

The products of Comparative Examples 1 and 2 also show substantially good dissolving abilities like the products of Examples, but all of the products of Examples 1 to 4 show more excellent dissolving abilities in the both initial dissolving ability and the dissolving ability after the storage and more specifically, they show not less than 50% of the 15 min values and not less than 75% of the 45 min values.

According to the present invention, the amount of the compound (A) as an effective component included in each individual dosage unit can be increased while maintaining the storage stability and particularly excellent dissolving ability. The pharmaceutical preparation of the present invention preferably contains not less than 100 mg, more preferably not less than 200 mg and particularly preferably 120 to 240 mg of the compound (A) and can be in the form of small tablets. More specifically, the present invention has such advantages that, when each tablet contains, for instance, 240 mg of the effective component, each tablet may have a mass on the order of 800 mg for the coating pharmaceutical preparation and that the pharmaceutical preparation shows such excellent dissolving ability and storage stability as shown in the foregoing Test Examples.

The pharmaceutical preparation of the present invention possesses an α 4-integrin-inhibitory action and accordingly, it is useful as a therapeutic agent or a prophylactic agent for treating or preventing either of inflammatory diseases, wherein the α 4-integrin-dependent leukocyte adhesion process is involved in the pathema, rheumatoid arthritis, inflammatory intestinal diseases, systemic lupus erythematosus, disseminated or multiple sclerosis, Sjogren's syndrome, asthma, psoriasis, allergy, diabetes (mellitus), cardiovascular diseases, arterial sclerosis, restenosis, tumor hyperplasia, tumor metastasis and graft rejection.

What is claimed is:
1. A pharmaceutical composition, comprising:
14 to 35% by mass, based on the total mass of the pharmaceutical composition, of a compound represented by the formula (A) or a pharmaceutically acceptable salt thereof dispersed in a matrix comprising 0.1 to 10 parts by mass of a water-soluble high molecular weight substance per one part by mass of the compound represented by the formula (A) or a pharmaceutically acceptable salt thereof,

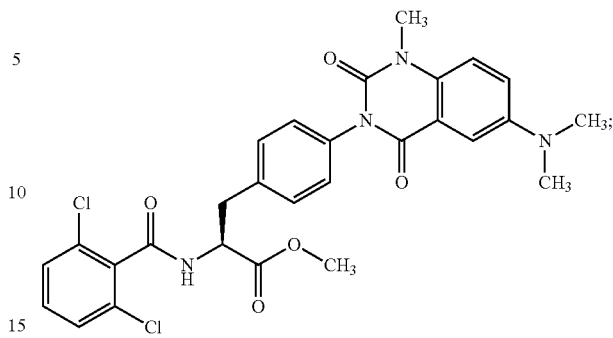

(A)

1 to 15% by mass, based on the total mass of the pharmaceutical composition, of Crospovidone; and
10 to 600 parts by mass, per 100 parts by mass of the Crospovidone, of sodium Cros-carmellose,
wherein the pharmaceutical composition is in the form of a tablet and comprises not less than 100 mg of the compound represented by the formula (A) or a pharmaceutically acceptable salt thereof.

2. The pharmaceutical composition of claim 1, wherein the water-soluble high molecular weight substance is at least one member selected from the group consisting of methyl cellulose, hypromellose, hydroxypropyl cellulose, hydroxypropyl-methyl cellulose phthalate, hydroxypropyl-methyl cellulose acetate succinate, carboxymethyl-ethyl cellulose, sodium carboxymethyl cellulose, hydroxyethyl cellulose, cellulose acetate phthalate, polyethylene glycol, polyvinyl alcohol, polyvinyl pyrrolidone, polyvinyl-acetal diethylamino acetate, aminoalkyl methacrylate copolymer E, aminoalkyl methacryl copolymer RS, methacrylic acid copolymer L, methacrylic acid copolymer LD, methacrylic acid copolymer S, carboxy vinyl polymer, gum Arabic, sodium alginate, alginic acid propylene glycol ester, agar, gelatin, tragacanth gum, and xanthane gum.

3. The pharmaceutical composition of claim 1, wherein the water-soluble high molecular weight substance is at least one member selected from the group consisting of methyl cellulose, hypromellose, hydroxypropyl cellulose, polyethylene glycol, polyvinyl alcohol and polyvinyl pyrrolidone.

4. The pharmaceutical composition of claim 1, which comprises a granulated product formed from a dispersion obtained by dispersing the compound represented by the formula (A) or a pharmaceutically acceptable salt thereof in the matrix, and Crospovidone.

5. The pharmaceutical composition of claim 1, further comprising:
an excipient.

6. The pharmaceutical composition of claim 5, wherein the excipient is at least one member selected from the group consisting of mannitol, pregelatinized starch and crystalline cellulose.

7. The pharmaceutical composition of claim 1, wherein the surface of the tablet is coated with a coating agent.

8. The pharmaceutical composition of claim 7, wherein the coating agent is at least one member selected from the group consisting of aminoalkyl methacrylate copolymer E, hypromellose, methyl cellulose, methyl-hydroxyethyl cellulose, Opadry, calcium carmellose, sodium carmellose, polyvinyl pyrrolidone, polyvinyl alcohol, dextrin, pullulan, gelatin, agar and gum Arabic.

9. The pharmaceutical composition of claim 1, wherein the water-soluble high molecular weight substance is methylcellulose.

10. The pharmaceutical composition of claim 1, which comprises 14 to 30.1% by mass, based on the total mass of the pharmaceutical composition, of the compound represented by the formula (A) or a pharmaceutically acceptable salt thereof, and 50 to 600 parts by mass, per 100 parts by mass of the Crospovidone, of sodium Cros-carmellose.

11. The pharmaceutical composition of claim 1, wherein the pharmaceutical composition comprises not less than 200 mg of the compound represented by the formula (A) or a pharmaceutically acceptable salt thereof.

12. The pharmaceutical composition of claim 1, wherein the pharmaceutical composition comprises 120 mg to 240 mg of the compound represented by the formula (A) or a pharmaceutically acceptable salt thereof.

13. A method of treating an inflammatory disease, comprising:
administering an effective amount of the pharmaceutical composition of claim 1 to a subject in need thereof.

14. A method of treating Crohn's disease, ulcerative colitis, systemic lupus erythematosus, disseminated or multiple sclerosis, Sjogren's syndrome, asthma, psoriasis, allergy, diabetes mellitus, cardiovascular diseases, arterial sclerosis, restenosis, tumor hyperplasia, tumor metastasis or graft rejection, comprising:
administering an effective amount of the pharmaceutical composition of claim 1 to a subject in need thereof.

15. The pharmaceutical composition of claim 1, further comprising:
partially pregelatinized starch;
crystalline cellulose; and
mannitol,
wherein the water-soluble high molecular weight substance is methyl cellulose.

16. The pharmaceutical composition of claim 10, further comprising:
partially pregelatinized starch;
crystalline cellulose; and
mannitol,
wherein the water-soluble high molecular weight substance is methyl cellulose.

17. The pharmaceutical composition of claim 1, further comprising:
pregelatinized starch;
crystalline cellulose; and
mannitol,
wherein the tablet is coated with a coating agent comprising hypromellose,
the water-soluble high molecular weight substance is methyl cellulose and is included in the matrix in an amount of 1 to 3 parts by mass per one part by mass of the compound represented by the formula (A) or a pharmaceutically acceptable salt thereof, and
an amount of the coating agent is 1 to 7% by mass, based on the total mass of the pharmaceutical composition.

* * * * *